(12) United States Patent
Hanatani (10) Patent No.: US 11,744,500 B2
(45) Date of Patent: Sep. 5, 2023

(54) INFORMATION PROCESSING APPARATUS AND NON-TRANSITORY COMPUTER READABLE MEDIUM

(71) Applicant: FUJIFILM BUSINESS INNOVATION CORP., Tokyo (JP)

(72) Inventor: Junji Hanatani, Kanagawa (JP)

(73) Assignee: FUJIFILM Business Innovation Corp., Tokyo (JP)

( * ) Notice: Subject to any disclaimer, the term of this patent is extended or adjusted under 35 U.S.C. 154(b) by 416 days.

(21) Appl. No.: 17/159,350

(22) Filed: Jan. 27, 2021

(65) Prior Publication Data

US 2022/0087586 A1 Mar. 24, 2022

(30) Foreign Application Priority Data

Sep. 23, 2020 (JP) .................................. 2020-158714

(51) Int. Cl.
| | |
|---|---|
| *A61B 5/22* | (2006.01) |
| *A61B 5/389* | (2021.01) |
| *A61B 5/11* | (2006.01) |
| *A61B 5/00* | (2006.01) |

(52) U.S. Cl.
CPC ............ *A61B 5/224* (2013.01); *A61B 5/1107* (2013.01); *A61B 5/1116* (2013.01); *A61B 5/1118* (2013.01); *A61B 5/1128* (2013.01); *A61B 5/389* (2021.01); *A61B 5/4519* (2013.01); *A61B 5/4523* (2013.01)

(58) Field of Classification Search
CPC ....... A61B 5/11; A61B 5/1104; A61B 5/1107; A61B 5/1113; A61B 5/1114; A61B 5/1115; A61B 5/1116; A61B 5/1117; A61B 5/1118; A61B 5/112; A61B 5/1121; A61B 5/1122; A61B 5/1123; A61B 5/1124; A61B 5/1126; A61B 5/1127; A61B 5/1128; A61B 5/224; A61B 5/313; A61B 5/389; A61B 5/4519; G06Q 10/06398

See application file for complete search history.

(56) References Cited

U.S. PATENT DOCUMENTS

2007/0256494 A1    11/2007   Nakamura et al.

FOREIGN PATENT DOCUMENTS

| JP | 2010-029340 A | 2/2010 |
|---|---|---|
| WO | 2005/122900 A1 | 12/2005 |

*Primary Examiner* — David J. McCrosky
(74) *Attorney, Agent, or Firm* — Oliff PLC (57) ABSTRACT

An information processing apparatus includes: a preparation device preparing information on a body posture; an acting force meter measuring a first acting force the body applies on a first object; a myoelectric potential meter; and a processor acquiring the information on the posture, acquiring information on the first acting force measured by the acting force meter, acquiring information on the myoelectric potential, setting an initial value for a second acting force the body applies to a second object other than the first object, estimating a muscle activity state corresponding to the posture, the first acting force, and the second acting force, repeating updating the second acting force such that a difference between (i) a muscle activity state determined based on the myoelectric potential and (ii) the estimated activity state decreases, and presenting the second acting force when the difference is less than a predetermined threshold value.

6 Claims, 5 Drawing Sheets

| BONE ID | BONE NAME | SHAPE DATA | RANGE OF MOTION DATA |
|---|---|---|---|
| B1 | ... | ... | ... |
| B2 | ... | ... | ... |
| ... | ... | ... | ... |

1211

| MUSCLE ID | MUSCLE NAME | ORIGIN POINT | INSERTION POINT |
|---|---|---|---|
| M1 | ... | ... | ... |
| M2 | ... | ... | ... |
| ... | ... | ... | ... |

1212

1213

| USER ID | USER NAME | PARAMETERS |
|---|---|---|
| U1 | ... | ... |
| U2 | ... | ... |
| ... | ... | ... |

| WORK ID | ACTING FORCE CONDITION |
|---|---|
| W1 | ... |
| W2 | ... |
| ... | ... |

| POSTURE CHANGE CONDITION | ACTING FORCE CONDITION |
|---|---|
| ... | ... |
| ... | ... |

INFORMATION PROCESSING APPARATUS AND NON-TRANSITORY COMPUTER READABLE MEDIUM

CROSS-REFERENCE TO RELATED APPLICATIONS

This application is based on and claims priority under 35 USC 119 from Japanese Patent Application No. 2020-158714 filed Sep. 23, 2020.

BACKGROUND

(i) Technical Field

The present disclosure relates to an information processing apparatus and a non-transitory computer readable medium.

(ii) Related Art

By analyzing a video recording of a worker, efficient work procedures of a skilled worker or characteristics of a wasteful work and a deviant movement of an unskilled worker are specified. For example, JP-A-2010-29340 discloses a human body movement evaluation device that evaluates a movement of a human body from a viewpoint of positioning accuracy. For example, WO 2005/122900 discloses a method and a device that calculate physiologically valid muscle tension using only non-invasively measurable movement data based on a musculoskeletal model.

SUMMARY

A final quality of processing or assembly at a production site often depends on an amount of applied force. However, it is difficult to read the amount of force from the video alone. In addition, it is not desirable to attach a measuring device to a point of action for which the processing or the like is performed in an actual work because the attaching of the measuring device affects the work itself.

Aspects of non-limiting embodiments of the present disclosure relate to estimating a force generated at a point of action based on (i) a force such as a load on a point other than the point of action, (ii) myoelectric potentials of a worker, (iii) and a posture of the worker without directly measuring the force.

Aspects of certain non-limiting embodiments of the present disclosure address the above advantages and/or other advantages not described above. However, aspects of the non-limiting embodiments are not required to address the advantages described above, and aspects of the non-limiting embodiments of the present disclosure may not address advantages described above.

According to an aspect of the present disclosure, there is provided an information processing apparatus including: a preparation device configured to prepare information on a posture of a body; an acting force meter configured to measure a first acting force that the body applies on a first object; a myoelectric potential meter configured to measure a myoelectric potential from a surface of the body; and a processor configured to: acquire the information on the posture prepared by the preparation device; acquire information on the first acting force measured by the acting force meter; acquire information on the myoelectric potential measured by the myoelectric potential meter; set an initial value for a second acting force that the body applies to a second object other than the first object; estimate a muscle activity state of the body corresponding to the posture, the first acting force, and the second acting force; repeat updating the second acting force such that a difference between (i) a muscle activity state determined based on the myoelectric potential and (ii) the estimated activity state decreases; and present the second acting force when the difference is less than a predetermined threshold value.

BRIEF DESCRIPTION OF THE DRAWINGS

Exemplary embodiment(s) of the present disclosure will be described in detail based on the following figures, wherein.

DETAILED DESCRIPTION

Exemplary Embodiment

Configuration of Information Processing Apparatus

Figure 1:
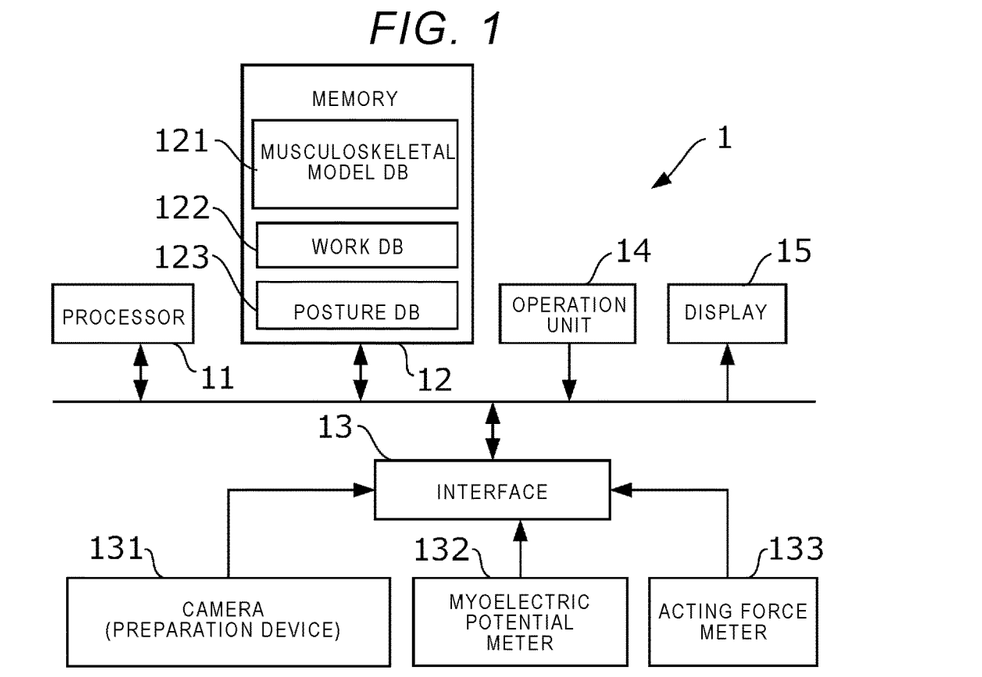
FIG. 1 is a diagram showing an example of a configuration of an information processing apparatus 1.

FIG. 1 is a diagram showing an example of a configuration of an information processing apparatus 1. The information processing apparatus 1 shown in FIG. 1 includes a processor 11, a memory 12, an interface 13, an operation unit 14, and a display 15. These units are communicably connected to each other via, for example, a bus.

The processor 11 controls each unit of the information processing apparatus 1 by reading and executing a program stored in the memory 12. The processor 11 is, for example, a central processing unit (CPU).

The operation unit 14 includes an operation element (such as operation buttons, a keyboard, a mouse, and a touch panel) for giving various instructions. The operation unit 14 receives an operation, and transmits a signal to the processor 11 according to an operation content thereof.

The display 15 displays a designated image under control of the processor 11. The display 15 shown in FIG. 1 includes a liquid crystal display which is a display screen for displaying the above image. A transparent touch panel of the operation unit 14 may be superposed on the liquid crystal display.

The interface 13 connects various devices to the processor 11 and causes the processor 11 to control those devices. The interface 13 shown in FIG. 1 connects a camera 131, a myoelectric potential meter 132, and an acting force meter 133 to the processor 11.

Figure 2:
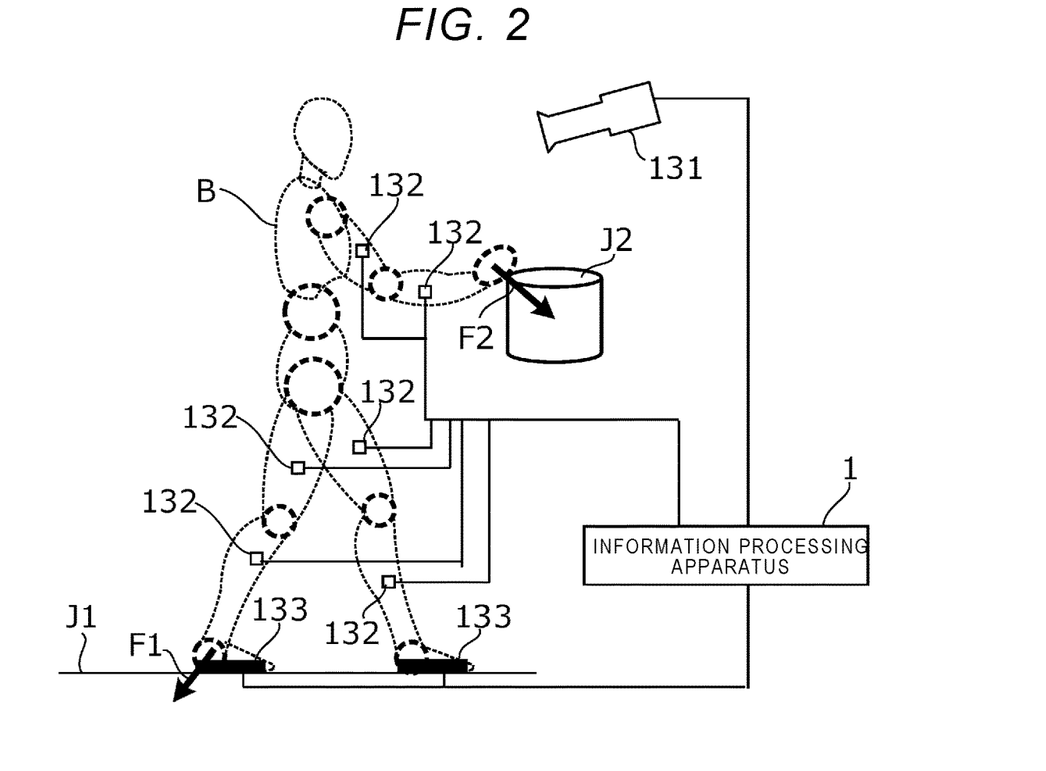
FIG. 2 is a diagram showing devices connected via an interface 13.

FIG. 2 is a diagram showing devices connected via the interface 13. The camera 131 is a digital still camera including an optical system such as a lens (not shown) and an image capturing device such as a charge coupled device (CCD) or a complementary metal oxide semiconductor (CMOS).

The camera 131 shown in FIG. 2 captures an image of a body B of a person under measurement and generates image data indicating the captured image. Then, the camera 131 supplies the generated image data to the processor 11 via the interface 13. The processor 11 extracts a contour of the body B from the image indicated by the image data acquired from the camera 131, and generates information on a posture of the body B. The processor 11 extracts the contour of the body B from the image, using, for example, an edge detection algorithm such as the Canny method. The processor 11 specifies the posture of the body B by applying a machine learning algorithm such as a convolutional neural network to the extracted contour of the body B.

Here, the "information on a posture" may be a position and an orientation of a head, shoulders, arms, torso, and feet of the person under measurement. The camera 131 is a video camera that periodically captures the body B. In this case, the processor 11 specifies a change in the posture of the body B from plural images captured periodically. That is, the camera 131 is an example of a preparation device that prepares information on the posture of the body B by capturing an appearance of the body B and generating image data indicating the appearance of the body B.

The camera 131 is not limited to the digital still camera as long as the camera 131 is a device that prepares the information on the posture of the body B. For example, the preparation device may be a contact type micro electro mechanical systems (MEMS) sensor or the like instead of the camera 131. In this case, the contact type MEMS sensors are attached to plural parts that do not affect the work on the body B of the person under measurement, and acceleration or the like of those parts is measured. Then, this contact type MEMS sensor may supply information such as the measured acceleration to the processor 11 as the "information on a posture".

Myoelectric potential meters 132 shown in FIG. 2 are, for example, myoelectric potential sensors, and are attached to a surface of the body B of the person under measurement. The myoelectric potential meters 132 measure myoelectric potentials of muscles under a skin at attached positions and supply signals indicating the myoelectric potentials to the processor 11. That is, the myoelectric potential meters 132 are examples of a myoelectric potential meter that measures the myoelectric potentials from the surface of the body.

Acting force meters 133 shown in FIG. 2 measure acting forces (referred to as a "first acting force") that the body B of the person under measurement applies on a surrounding object (referred to as a "first object"). That is, the acting force meters 133 are examples of an acting force meter that measures the first acting force that the body applies to the first object. The acting force meters 133 are, for example, load sensors. The acting force meter 133 measure a first acting force F1 acting on a ground J1 as the first object. This first acting force F1 is, that is, a force with which the person under measurement steps on the ground J1 or the like.

The acting force meters 133 shown in FIG. 2 are, for example, accommodated in shoes. The acting force meter 133 measures the first acting force when a sole (a part of the body B) of the person under measurement presses against the ground J1. The acting force meter 133 may be accommodated on a seat surface of a seat on which the person under measurement sits when the person under measurement works in a sitting position. In this case, the acting force meter 133 measures the first acting force when buttocks (a part of the body B) of the person under measurement press the seat surface, as the first object. That is, the first object is an object (such as the ground and the seat surface) that is present around the person under measurement but is not a target of the work. Since the first object is the object that is not the target of the work, the first acting force acting on the first object is directly measured by the acting force meter 133.

A product J2 shown in FIG. 2 is an object (referred to as a "second object") that is the target for which the person under measurement performs the above work. The product J2 is, for example, a connector for a cable such as a harness. In this case, the above work is to insert the connector and connect the connector and the cable to each other. The person under measurement shown in FIG. 2 uses hands of the body B to perform the work (such as processing) on the product J2. The hands of the person under measurement exert an acting force (referred to as a "second acting force") on the second object.

The product J2 shown in FIG. 2 receives the second acting force F2 from the hands of the person under measurement. At this time, it is possible to attach the myoelectric potential meters 132 to surfaces of the hands that touch the product J2 because workability is relatively not impaired.

However, it is not desirable to attach the acting force meters 133 configured to measure the acting force to the product J2 itself because the work may be significantly hindered.

A muscle tension does not necessarily reflect the acting force exerted on a work target. For example, when a worker holds a tool tightly, muscle tensions generated by plural competing muscles cancel each other in the tool. Therefore, any of these muscle tensions is not converted into a momentum of the work target, and an appearance of the work target may also be the same as that when no acting force is exerted thereon.

That is, it is often difficult to know a direction of an adjusted force, a magnitude of a strain, or the like from a state of the hands captured by the camera 131. Therefore, it is difficult to directly measure the second acting force F2. The information processing apparatus 1 estimates this second acting force F2.

The memory 12 shown in FIG. 1 is a storage that stores an operating system, various programs, data, and the like to be read into the processor 11. The memory 12 includes a random access memory (RAM) and a read only memory (ROM). The memory 12 may include a solid state drive, a hard disk drive, or the like. The memory 12 also stores a musculoskeletal model DB 121, a work DB 122, and a posture DB 123.

Figure 3:
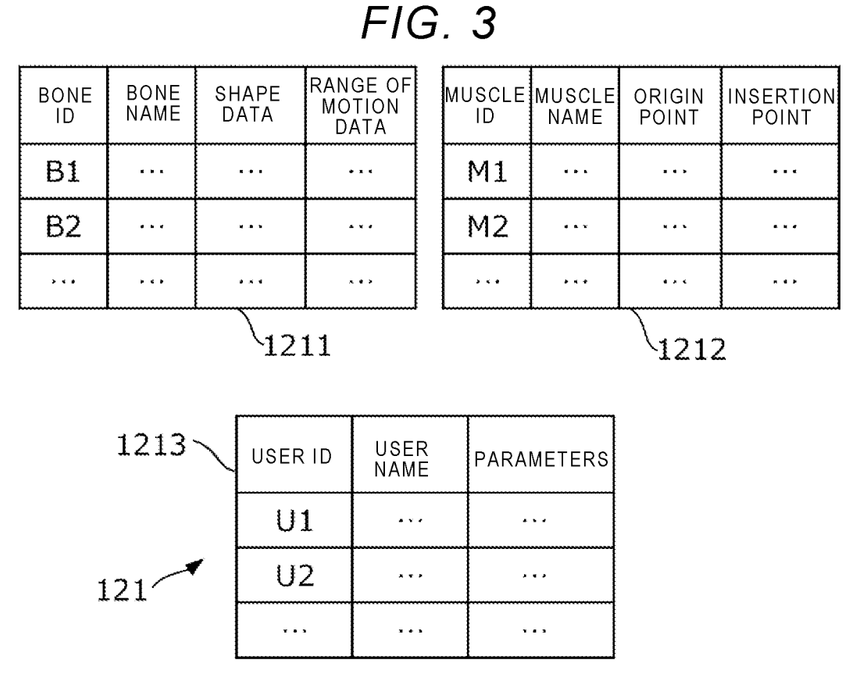
FIG. 3 is a diagram showing an example of a musculoskeletal model DB 121.

FIG. 3 is a diagram showing an example of the musculoskeletal model DB 121. The musculoskeletal model DB 121 is a database that stores physical models of bones and muscles. The musculoskeletal model DB 121 shown in FIG. 3 includes a bone model table 1211, a muscle model table 1212, and a user table 1213.

The bone model table 1211 is a table that describes information on the bones of the human body. The bone model table 1211 shown in FIG. 3 includes items of a bone ID, a bone name, shape data, and a range of motion data. The bone ID is identification information that identifies a bone of the human body. The bone name is a name of a bone identified by a corresponding bone ID. The shape data is data obtained by quantifying a shape of a bone identified by a corresponding bone ID in a three-dimensional space. The range of motion data is data that quantifies a range (referred to as a "range of motion") where a bone identified by a corresponding bone ID moves. The information processing apparatus 1 specifies, for example, shapes or ranges of motion of bones of a standard human body with reference to the bone model table 1211.

The muscle model table 1212 is a table that describes information on the muscles of the human body. The muscle model table 1212 shown in FIG. 3 includes items of a muscle ID, a muscle name, an origin point, and an insertion point. The muscle ID is identification information that identifies a muscle of the human body. The muscle name is a name of a muscle identified by a corresponding muscle ID. The origin point is a position of a bone to which the muscle identified by the corresponding muscle ID is attached, and is a point where the muscle is attached to the bone that does not move in response to a movement of the muscle. The insertion point is a position of the bone to which the muscle identified by the corresponding muscle ID is attached, and is a point where the muscle is attached to the bone that moves due in response to a movement of the muscle. There may be plural origin points and plural insertion points for one muscle. The information processing apparatus 1 specifies, for example, a position of a bone to which a muscle of a standard human body is attached and a bone moved by the muscle with reference to the muscle model table 1212.

The user table 1213 is a table that describes information on bones and muscles unique to each user who is the person under measurement. The user table 1213 shown in FIG. 3 includes items of a user ID, a user name, and parameters. The user ID is identification information that identifies each person under measurement. The user name is a name of a user identified by a corresponding user ID. The parameters refer to various numerical values indicating bones and muscles unique to the user identified by the corresponding user ID.

The parameters may include, for example, a factor by which the shape data of the bone is multiplied to calculate a size of the bone of an individual user. Further, the parameters may include, for example, a maximum value of a tension (referred to as a "muscle tension") output by the muscle of the individual user. The parameters may be numerical values, nominal scales, or the like that indirectly indicate the information on the bones and the muscles of the user. For example, the parameters may include information such as a gender, an age, and genetic characteristics of the user. The information processing apparatus 1 specifies, for example, (i) characteristics such as laterality and strain of the bones and the muscles of the user and (ii) an ability such as an instantaneous force and endurance, with reference to the user table 1213, the bone model table 1211, and the muscle model table 1212 described above.

Figure 4:
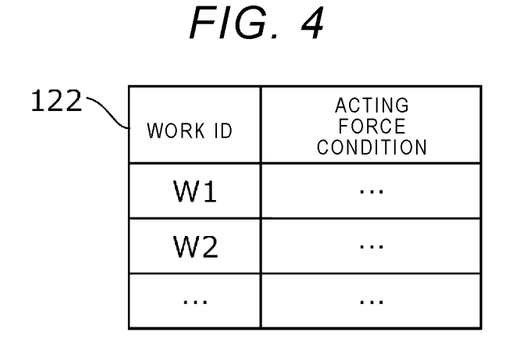
FIG. 4 is a diagram showing an example of a work DB 122.

FIG. 4 is a diagram showing an example of the work DB 122. The work DB 122 is a database that stores information on a work to be performed by a body in association with conditions imposed on an acting force generated by the work. The work DB 122 shown in FIG. 4 stores a work ID and an acting force condition in association with each other.

The work ID is identification information that identifies a work performed by the person under measurement. The acting force condition is a condition under which the body of the person under measurement constrains the second acting force acting on the second object that is the target of the work when the person under measurement performs the work identified by the corresponding work ID. The acting force condition is, for example, ranges of a direction and a magnitude of the second acting force.

The acting force is generally a vector quantity having six degrees of freedom, including (i) a translational force indicated in a combination of an x-axis direction, a y-axis direction, and a z-axis direction and (ii) a rotational moment indicated in a combination of a yaw, a pitch, and a roll. However, for example, when the work performed by the person under measurement is a work of inserting a connector, the direction of the second acting force that the body of the person under measurement applies to the connector (which is the second object) is simply be an insertion direction of this connector. Further, it can be seen from a physical configuration of the connector, statistical data of an insertion work, and the like that the magnitude of the second acting force is also within a certain range.

That is, when a work content is known in advance, the direction and the magnitude of the second acting force can be roughly estimated. The information processing apparatus 1 may store calculated data of the magnitude and the direction of the second acting force in the memory 12 together with the work content at that time. Then, the processor 11 may use the magnitude and direction data stored in the memory 12 as a constraint condition when searching for an optimum value of a new second acting force.

The information processing apparatus 1 acquires the information on the work to be performed by the body in advance, and refers to the work DB 122 and specifies the acting force condition that is determined based on the acquired information on the work as a condition that the second acting force is to satisfy.

Figure 5:
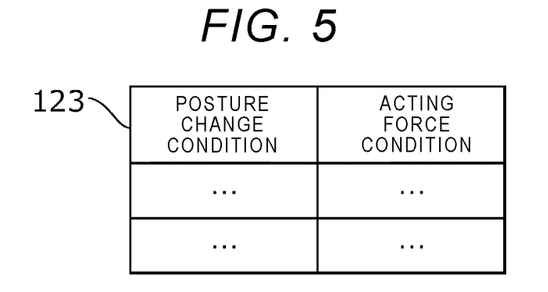
FIG. 5 is a diagram showing an example of a posture DB 123.

FIG. 5 is a diagram showing an example of the posture DB 123. The posture DB 123 is a database that stores a condition that a second acting force that is generated when the posture changes is to satisfy. The posture DB 123 stores the condition for each type of change. The posture DB 123 shown in FIG. 5 stores a posture change condition and the acting force condition in association with each other.

The posture change conditions are conditions used to classify changes of the posture of the body into the types of change. The acting force condition is a condition that constrains the second acting force when the posture that satisfies a corresponding posture change condition changes.

For example, when the body changes to a crouching posture, it becomes impossible to perform certain movements while standing up. Further, for example, when the body changes to a stepping posture in which a torso is pushed forward with a foot pulled backward, it becomes impossible to perform a movement of pulling the second object that is held in the hands.

That is, when the posture of the body changes, the condition that a body movement is to satisfy is determined according to the change of the posture. Then, the acting force condition indicating the ranges of the direction and magnitude of the second acting force is determined according to the condition that the body movement is to satisfy. That is, the posture DB 123 stores the condition that constrains the second acting force so as to satisfy a condition of a body movement determined based on information on the change in the posture.

With reference to the posture DB 123, the information processing apparatus 1 searches the posture change conditions for, for example, a condition satisfied by a change of the information on the posture of the body prepared by the camera 131, and specifies the acting force condition stored in association with the found posture change condition as a condition that the second acting force is to satisfy.

Functional Configuration of Information Processing Apparatus

Figure 6:
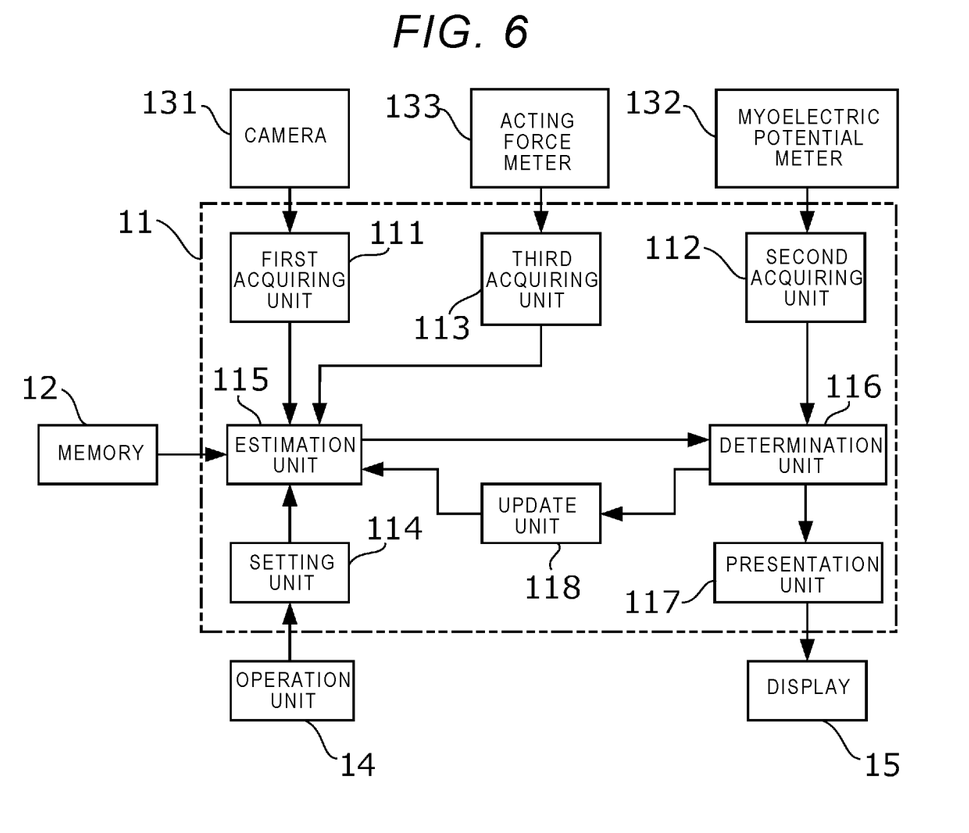
FIG. 6 is a diagram showing an example of a functional configuration of the information processing apparatus 1.

FIG. 6 is a diagram showing an example of a functional configuration of the information processing apparatus 1. The processor 11 of the information processing apparatus 1 serves as a first acquiring unit 111, a second acquiring unit 112, a third acquiring unit 113, a setting unit 114, an estimation unit 115, a determination unit 116, a presentation unit 117, and an update unit 118, by executing the program stored in the memory 12.

The first acquiring unit 111 acquires the information on the posture of the body B prepared by the camera 131 which is the example of the preparation device. The information acquired by the first acquiring unit 111 is, for example, image data indicating images periodically captured by the camera 131.

The second acquiring unit 112 acquires information on the myoelectric potentials measured by the myoelectric potential meter 132. The third acquiring unit 113 acquires information on the first acting force measured by the acting force meter 133.

The setting unit 114 receives an operation of a user who is an operator via the operation unit 14 and sets an initial value for the second acting force that the body B applies to the second object according to a content of the operation thereof. The setting unit 114 may set the initial value stored in the memory 12 in advance as the second acting force. In this case, the information processing apparatus 1 may not include the operation unit 14.

The estimation unit 115 estimates a muscle activity state of the body B corresponding to (i) the posture indicated by the information acquired by the first acquiring unit 111, (ii) the first acting force indicated by the information acquired by the third acquiring unit 113, and (iii) the second acting force whose initial value is set by the setting unit 114. This estimation is performed by referring to the musculoskeletal model DB 121 stored in the memory 12. That is, the estimation unit 115 estimates the muscle activity state when the body B is at the above described posture and applies the first acting force described above to the first object such as the ground J1 and applies the second acting force described above to the second object of the product J2.

In order to perform the above estimation, the estimation unit 115 performs inverse dynamics calculation using (i) the posture indicated by the information acquired by the first acquiring unit 111, (ii) the first acting force indicated by the information acquired by the third acquiring unit 113, and (iii) the second acting force set by the initial value obtained by the setting unit 114. The estimation unit 115 may use, for example, a heuristic method such as a genetic algorithm to perform the above estimation.

The determination unit 116 calculates a difference between (i) the muscle activity state of the body B determined based on the myoelectric potentials indicated by the information acquired by the second acquiring unit 112 and (ii) the muscle activity state estimated by the estimation unit 115. Then, the determination unit 116 determines whether the calculated difference exceeds a threshold value.

When the determination unit 116 determines that the above difference does not exceed the threshold value, the presentation unit 117 presents the second acting force used by the estimation unit 115 for the estimation on the display 15. That is, the presentation unit 117 presents the second acting force when the above difference is less than the threshold value.

When the determination unit 116 determines that the above difference exceeds the threshold value, the update unit 118 updates the second acting force used by the estimation unit 115 for the estimation such that this difference decreases. The update unit 118 repeats this update when the determination unit 116 determines that the above difference exceeds the threshold value. The second acting force updated by the update unit 118 is used again for the estimation by the estimation unit 115. In order to perform the above update, the update unit 118 may use, for example, an optimization algorithm using a functional gradient such as the steepest descent method, the Newton-Rapson method, or the downhill simplex method.

Operation of Information Processing Apparatus

Figure 7:
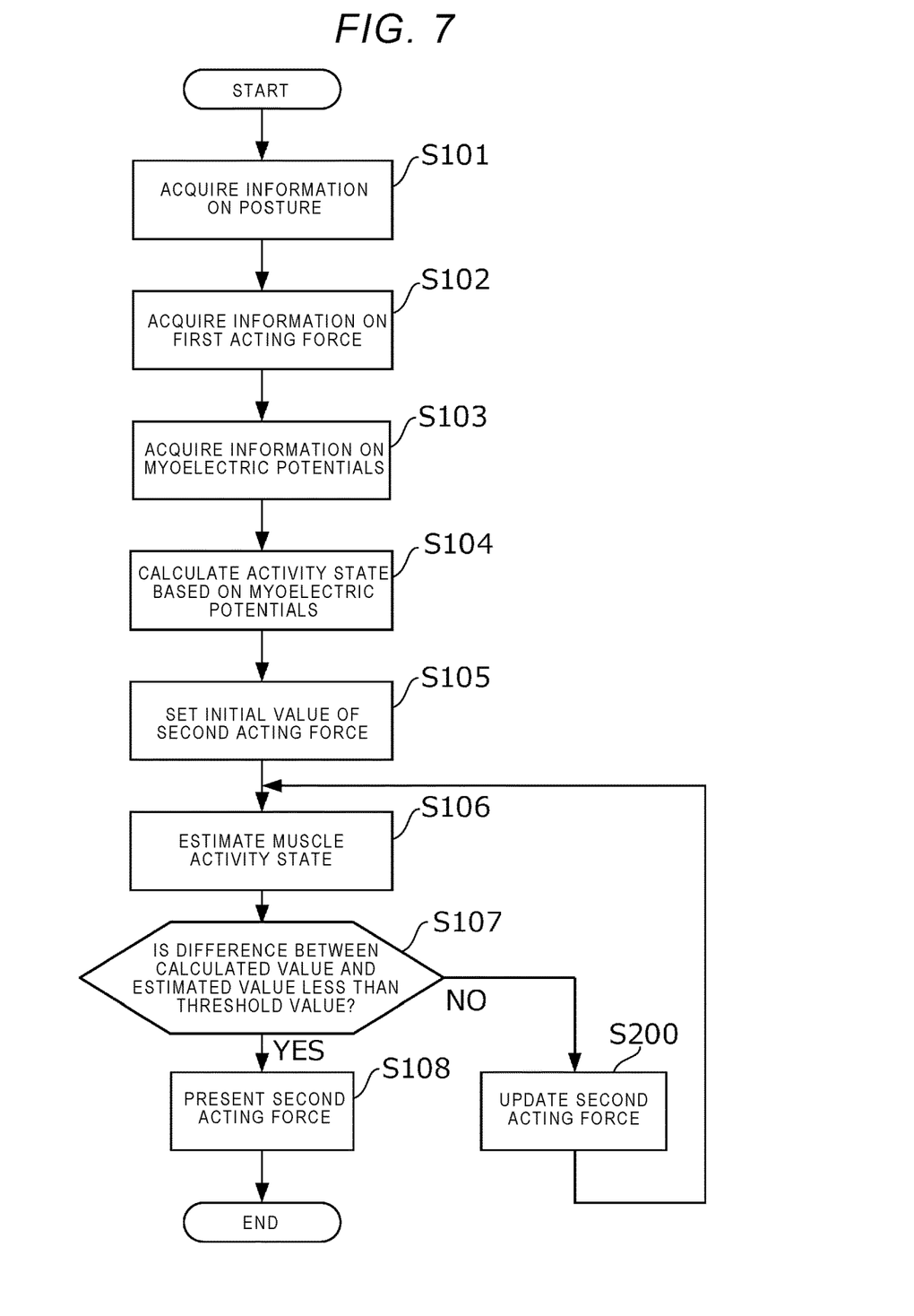
FIG. 7 is a flowchart of an example of an operation of the information processing apparatus 1.

FIG. 7 is a flowchart of an example of an operation of the information processing apparatus 1. The processor 11 of the information processing apparatus 1 acquires the information on the posture from the camera 131 via the interface 13 (step S101). The processor 11 acquires the information on the first acting force from the acting force meter 133 via the interface 13 (step S102). The processor 11 acquires the information on the myoelectric potentials from the myoelectric potential meter 132 via the interface 13 (step S103).

The processor 11 calculates the muscle activity state based on the acquired myoelectric potentials (step S104). Then, the processor 11 sets the initial value of the second acting force according to the operation of the user received via the operation unit 14, for example (step S105).

The processor 11 applies the posture of the body B of the person under measurement and the first acting force which are indicated by the acquired information and the second acting force whose initial value is set to the musculoskeletal model DB 121 stored in the memory 12, and estimates the muscle activity state of the body B (step S106).

Then, the processor 11 obtains the difference between the activity state (that is, a calculated value) calculated in step S104 and the activity state (that is, an estimated value) estimated in step S106, and determines whether this difference is less than the threshold value (step S107).

The measured myoelectric potential may be used as the muscle activity state. Alternatively, a muscle activity state of a muscle in interest may be calculated or estimated based on a ratio of a measured value of the muscle activity state of the muscle in interest to a maximum muscle activity state of the muscle in interest.

When determining that the above difference is less than the threshold value (step S107, YES), the processor 11 presents the second acting force used for the estimation (step S108) and ends the processing.

On the other hand, when determining that the above difference is not less than the threshold value (step S107, NO), the processor 11 updates the second acting force used for the estimation (step S200) and returns the processing to step S106.

Figure 8:
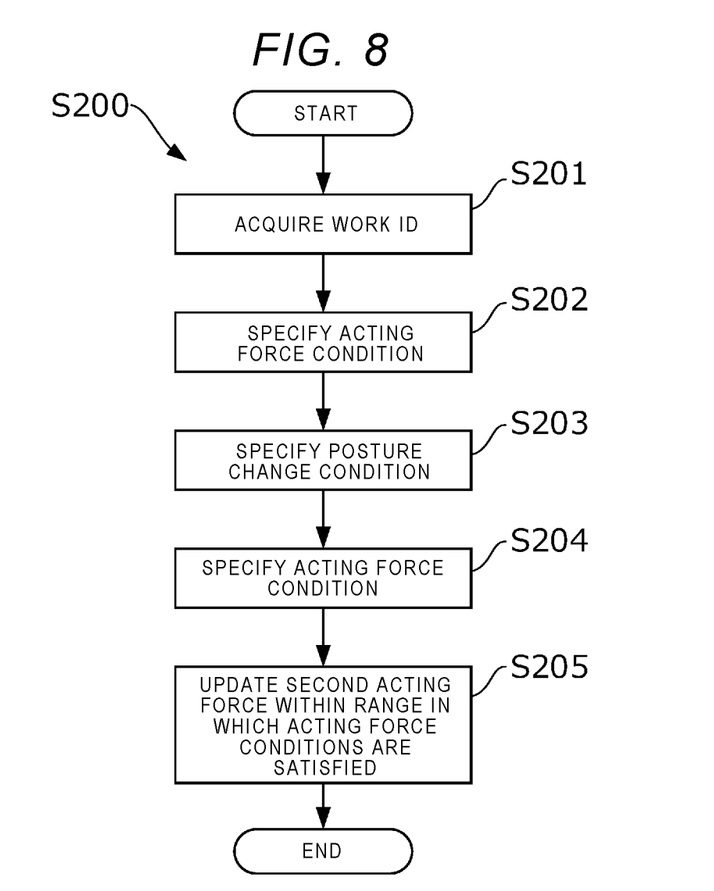
FIG. 8 is a flowchart of an example of an operation for updating a second acting force.

FIG. 8 is a flowchart of an example of an operation for updating the second acting force. The processor 11 acquires the work ID indicating the work performed by the person under measurement (step S201), and searches the work DB 122 for the acting force condition corresponding to the work ID and specifies the acting force condition corresponding to the work ID (step S202).

The processor 11 specifies the posture change condition satisfied by a change with time of the information on the posture (step S203), and specifies the acting force condition associated with the posture change condition in the posture DB 123 (step S204).

The processor 11 updates the second acting force within a range in which both the acting force conditions specified in step S202 and step S204 are satisfied (step S205).

The acting force condition specified in step S202 is a condition that constrains the direction and magnitude of the second acting force based on the content of the work. Therefore, the acting force condition excludes, for example, a second acting force having a direction or a magnitude that cannot occur when the work is performed, from an update target. As a result, a search for the optimum value of the second acting force by the information processing apparatus 1 is prevented from falling into an erroneous local solution, and a speed of the search is improved.

The acting force condition specified in step S204 is a condition that constrains the direction and magnitude of the second acting force based on the change in the posture of the body B. Therefore, the acting force condition excludes, for example, a second acting force having a direction or a magnitude that cannot occur when the posture changes, from the update target. As a result, a search for the optimum value of the second acting force by the information processing apparatus 1 is prevented from falling into an erroneous local solution, and a speed of the search is improved.

By the above operation, the information processing apparatus 1 estimates a force generated at a point of action based on (i) a force such as a load generated at a point other than the point of action, (ii) the myoelectric potentials of the worker, and (iii) the posture of the worker, without directly measuring the force.

Modifications

The above is the description of the exemplary embodiment, and this exemplary embodiment may be modified as follows. In addition, the following modifications may be combined with each other.

<1>

In the above exemplary embodiment, the information processing apparatus 1 includes the processor 11 configured with the CPU. Alternatively, a controller that controls the information processing apparatus 1 may have another configuration. For example, the information processing apparatus 1 may include various processors or the like in addition to the CPU.

In the embodiments above, the term "processor" refers to hardware in a broad sense. Examples of the processor include general processors (e.g., CPU: Central Processing Unit) and dedicated processors (e.g., GPU: Graphics Processing Unit, ASIC: Application Specific Integrated Circuit, FPGA: Field Programmable Gate Array, and programmable logic device).

<2>

In the embodiments above, the term "processor" is broad enough to encompass one processor or plural processors in collaboration which are located physically apart from each other but may work cooperatively.

The order of operations of the processor is not limited to one described in the embodiments above, and may be changed.

<3>

In the above exemplary embodiment, when the second acting force is updated, the processor 11 searches the work DB 122 for the acting force condition corresponding to the work ID and specifies the acting force condition corresponding to the work ID. However, the processor 11 may not specify this acting force condition. In this case, the information processing apparatus 1 may not store the work DB 122 in the memory 12.

<4>

In the above exemplary embodiment, the processor 11 specifies the posture change condition satisfied by the change with time of the information on the posture when the second acting force is updated, and specifies the acting force condition associated with the posture change condition in the posture DB 123. However, the processor 11 may not specify this acting force condition. In this case, the information processing apparatus 1 may not store the posture DB 123 in the memory 12.

<5>

In the above exemplary embodiment, the program executed by the processor 11 of the information processing apparatus 1 is an example of a program that causes a computer including a preparation device configured to prepare information on a posture of a body, an acting force meter configured to measure a first acting force that the body applies on a first object, a myoelectric potential meter configured to measure a myoelectric potential from a surface of the body, and a processor, to execute: acquiring the information on the posture prepared by the preparation device; acquiring information on the first acting force measured by the acting force meter; acquiring information on the myoelectric potential measured by the myoelectric potential meter; setting an initial value for a second acting force that the body applies to a second object other than the first object; estimating a muscle activity state of the body corresponding to the posture, the first acting force, and the second acting force; repeating updating the second acting force such that a difference between (i) a muscle activity state determined based on the myoelectric potential and (ii) the estimated activity state decreases; and presenting the second acting force when the difference is less than a predetermined threshold value.

This program may be provided in a state of being stored in a computer readable recording medium, such as a magnetic recording medium (for example, a magnetic tape and a magnetic disk), an optical recording medium (for example, an optical disc), an magneto-optical recording medium, and a semiconductor memory. Further, the program may be downloaded via a communication line such as the Internet.

The foregoing description of the exemplary embodiments of the present disclosure has been provided for the purposes of illustration and description. It is not intended to be exhaustive or to limit the disclosure to the precise forms disclosed. Obviously, many modifications and variations will be apparent to practitioners skilled in the art. The embodiments were chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. An information processing apparatus comprising:
 a preparation device configured to prepare information on a posture of a body;
 an acting force meter configured to measure a first acting force that the body applies on a first object;
 a myoelectric potential meter configured to measure a myoelectric potential from a surface of the body; and
 a processor configured to:
  acquire the information on the posture prepared by the preparation device;
  acquire information on the first acting force measured by the acting force meter;
  acquire information on the myoelectric potential measured by the myoelectric potential meter;
  set an initial value for a second acting force that the body applies to a second object other than the first object;

estimate a muscle activity state of the body corresponding to the posture, the first acting force, and the second acting force;

repeat updating the second acting force such that a difference between (i) a muscle activity state determined based on the myoelectric potential and (ii) the estimated activity state decreases; and present the second acting force when the difference is less than a predetermined threshold value.

2. The information processing apparatus according to claim 1, wherein the processor is configured to:

acquire information on a work to be performed by the body in advance; and repeat the updating the second acting force such that (i) a condition determined based on the information on the work is satisfied and (ii) the difference decreases.

3. The information processing apparatus according to claim 2, wherein the processor is configured to:

acquire information on a change in the posture; and repeat the updating the second acting force such that (i) a condition of a body movement determined based on the information on the change in the posture is satisfied and (ii) the difference decreases.

4. The information processing apparatus according to claim 1, wherein the processor is configured to:

acquire information on a change in the posture; and repeat the updating the second acting force such that (i) a condition of a body movement determined based on the information on the change in the posture is satisfied and (ii) the difference decreases.

5. A non-transitory computer readable medium storing a program that causes a computer to execute information processing, the computer including a preparation device configured to prepare information on a posture of a body, an acting force meter configured to measure a first acting force that the body applies on a first object, a myoelectric potential meter configured to measure a myoelectric potential from a surface of the body, and a processor, the information processing comprising:

acquiring the information on the posture prepared by the preparation device;

acquiring information on the first acting force measured by the acting force meter;

acquiring information on the myoelectric potential measured by the myoelectric potential meter;

setting an initial value for a second acting force that the body applies to a second object other than the first object;

estimating a muscle activity state of the body corresponding to the posture, the first acting force, and the second acting force;

repeating updating the second acting force such that a difference between (i) a muscle activity state determined based on the myoelectric potential and (ii) the estimated activity state decreases; and presenting the second acting force when the difference is less than a predetermined threshold value.

6. An information processing apparatus comprising:

preparation means for preparing information on a posture of a body;

acting force means for measuring a first acting force that the body applies on a first object;

myoelectric potential means for measuring a myoelectric potential from a surface of the body; and means for acquiring the information on the posture prepared by the preparation means;

acquiring information on the first acting force measured by the acting force means;

acquiring information on the myoelectric potential measured by the myoelectric potential means;

setting an initial value for a second acting force that the body applies to a second object other than the first object;

estimating a muscle activity state of the body corresponding to the posture, the first acting force, and the second acting force;

repeating updating the second acting force such that a difference between (i) a muscle activity state determined based on the myoelectric potential and (ii) the estimated activity state decreases; and presenting the second acting force when the difference is less than a predetermined threshold value.

* * * * *